United States Patent
Jorgensen et al.

(10) Patent No.: US 8,961,449 B2
(45) Date of Patent: Feb. 24, 2015

(54) TAMPON INSERTION DEVICE FOR IMPROVED CONTROL AND PLEDGET PLACEMENT

(75) Inventors: Robert Jorgensen, Middletown, DE (US); Keith Edgett, Middletown, DE (US); Eugene P. Dougherty, Jr., Camden-Wyoming, DE (US)

(73) Assignee: Eveready Battery Company, Inc., St. Louis, MO (US)

( * ) Notice: Subject to any disclaimer, the term of this patent is extended or adjusted under 35 U.S.C. 154(b) by 0 days.

(21) Appl. No.: 11/890,138

(22) Filed: Aug. 3, 2007

(65) Prior Publication Data

US 2008/0119778 A1    May 22, 2008

Related U.S. Application Data

(60) Provisional application No. 60/835,638, filed on Aug. 4, 2006.

(51) Int. Cl.
*A61F 13/26* (2006.01)
*A61F 13/32* (2006.01)

(52) U.S. Cl.
USPC ............................ 604/13; 604/15; 604/385.17

(58) Field of Classification Search
USPC ........................................ 604/11–18, 385.17
See application file for complete search history.

(56) References Cited

U.S. PATENT DOCUMENTS

| | | | | |
|---|---|---|---|---|
| 1,794,221 A | * | 2/1931 | Washburn et al. | 604/15 |
| 3,086,527 A | * | 4/1963 | Forrest | 604/15 |
| 3,148,680 A | * | 9/1964 | Roberts et al. | 604/18 |
| 4,048,998 A | * | 9/1977 | Nigro | 604/14 |
| D250,663 S | * | 12/1978 | Koch et al. | D24/141 |
| 5,395,308 A | * | 3/1995 | Fox et al. | 604/15 |
| 5,437,628 A | * | 8/1995 | Fox et al. | 604/14 |
| 6,248,089 B1 | * | 6/2001 | Porat | 604/17 |
| 6,264,626 B1 | * | 7/2001 | Linares et al. | 604/15 |
| 6,264,972 B1 | | 7/2001 | Drury | |
| 6,368,442 B1 | * | 4/2002 | Linares et al. | 156/198 |
| 6,423,025 B1 | * | 7/2002 | Buzot | 604/15 |
| 6,478,764 B1 | * | 11/2002 | Suga | 604/15 |
| 6,511,452 B1 | * | 1/2003 | Rejai et al. | 604/15 |

(Continued)

FOREIGN PATENT DOCUMENTS

| | | |
|---|---|---|
| CA | 2608673 | 12/2004 |
| EP | 1040808 A2 | 10/2000 |

(Continued)

OTHER PUBLICATIONS

Definition of "flare", Merriam Webster On Line.*

(Continued)

*Primary Examiner* — Melanie Hand
*Assistant Examiner* — Paula Craig
(74) *Attorney, Agent, or Firm* — Energizer Personal Care, LLC

(57) ABSTRACT

A tampon applicator assembly has a barrel with a fingergrip. The fingergrip has one or more flared portions and/or one or more rib-like or ring-like gripping structures. A tampon applicator fingergrip includes one or more flared portions having a flare angle between about 139° and about 156° and a curve represented by an equation range of $y=16.127x^3-1.5061x^2+0.0568x+0.0001$ to $y=6.9136x^3-0.5598x^2+0.0168x+0.0003$, where y is an incremental increase in a height of the curve at a distance along a length of the curve.

12 Claims, 13 Drawing Sheets

(56) References Cited

U.S. PATENT DOCUMENTS

| | | | |
|---|---|---|---|
| 6,648,846 B2 * | 11/2003 | Binner et al. | 604/15 |
| 6,673,032 B2 * | 1/2004 | Buzot | 604/15 |
| D492,033 S * | 6/2004 | Jarmon et al. | D24/141 |
| 6,890,324 B1 * | 5/2005 | Jackson et al. | 604/385.17 |
| D511,572 S * | 11/2005 | Weber et al. | D24/141 |
| D512,142 S * | 11/2005 | Weber et al. | |
| D515,212 S * | 2/2006 | Edgett et al. | D24/141 |
| D517,691 S * | 3/2006 | Turchi et al. | D24/141 |
| D517,692 S * | 3/2006 | Weber et al. | D24/141 |
| 7,044,928 B2 * | 5/2006 | LeMay et al. | 604/15 |
| 7,141,036 B2 * | 11/2006 | Berman et al. | 604/60 |
| D559,983 S * | 1/2008 | Edgett et al. | D24/141 |
| 2002/0010413 A1 * | 1/2002 | Binner et al. | 604/15 |
| 2002/0138035 A1 * | 9/2002 | Hull, Jr. | 604/18 |
| 2002/0188283 A1 * | 12/2002 | Binner et al. | 604/904 |
| 2002/0193726 A1 * | 12/2002 | Cimber | 604/11 |
| 2003/0036721 A1 | 2/2003 | Zhao et al. | |
| 2003/0236485 A1 * | 12/2003 | Fedyk et al. | 604/11 |
| 2004/0054317 A1 * | 3/2004 | Lemay et al. | 604/15 |
| 2004/0199100 A1 * | 10/2004 | LeMay et al. | 604/11 |
| 2004/0199101 A1 * | 10/2004 | LeMay et al. | 604/11 |
| 2004/0199102 A1 * | 10/2004 | LeMay et al. | 604/11 |
| 2005/0038373 A1 * | 2/2005 | Avery et al. | 604/11 |
| 2007/0032758 A1 * | 2/2007 | Chase et al. | 604/12 |
| 2008/0033337 A1 * | 2/2008 | Dougherty et al. | 604/15 |

FOREIGN PATENT DOCUMENTS

| | | | |
|---|---|---|---|
| GB | 2166656 A * | 5/1986 | |
| JP | 2000-279446 | 10/2000 | |
| JP | 2005-504570 | 2/2005 | |
| JP | 2005-530557 | 10/2005 | |
| JP | 2005-538777 | 12/2005 | |
| WO | WO 01/00127 A1 | 1/2001 | |

OTHER PUBLICATIONS

International Search Report for International Application No. PCT/US07/17390 dated Jun. 4, 2008.

Written Opinion for International Application No. PCT/US07/17390 dated Jun. 4, 2008.

Korean Office Action dated Feb. 8, 2001 from corresponding Korean Patent Application No. 10-2009-7002304.

Extended European Search Report dated Apr. 18, 2011 for corresponding European Patent Application No. 07836497.3.

Canadian Office Action dated Jan. 24, 2011 for corresponding Canadian Patent Application No. 2,659,887.

Japanese Office Action dated Jul. 19, 2011 from corresponding Japanese Patent Application No. 2009-523794.

Canadian Office Action Dated Aug. 24, 2012 From Corresponding Canadian Application No. 2,779,057.

European Examination Report Dated Jun. 11, 2012 From Corresponding European Application No. 07 836 497.3-2124.

Japanese Office Action Dated Jul. 31, 2012 From Corresponding Japanese Application No. 2009-523794.

Second Official Action mailed Oct. 12, 2012 for corresponding Colombian Patent Application No. 09.012.639 with English summary.

* cited by examiner

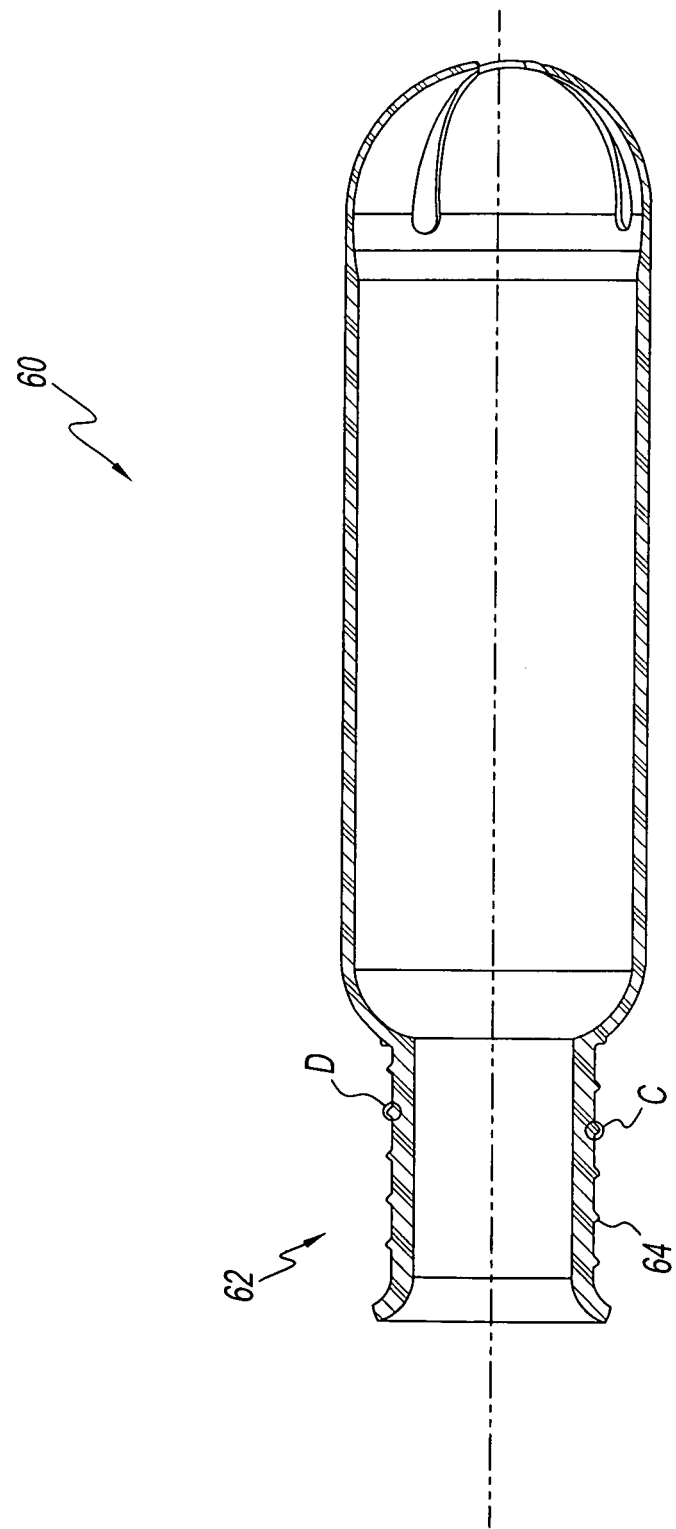

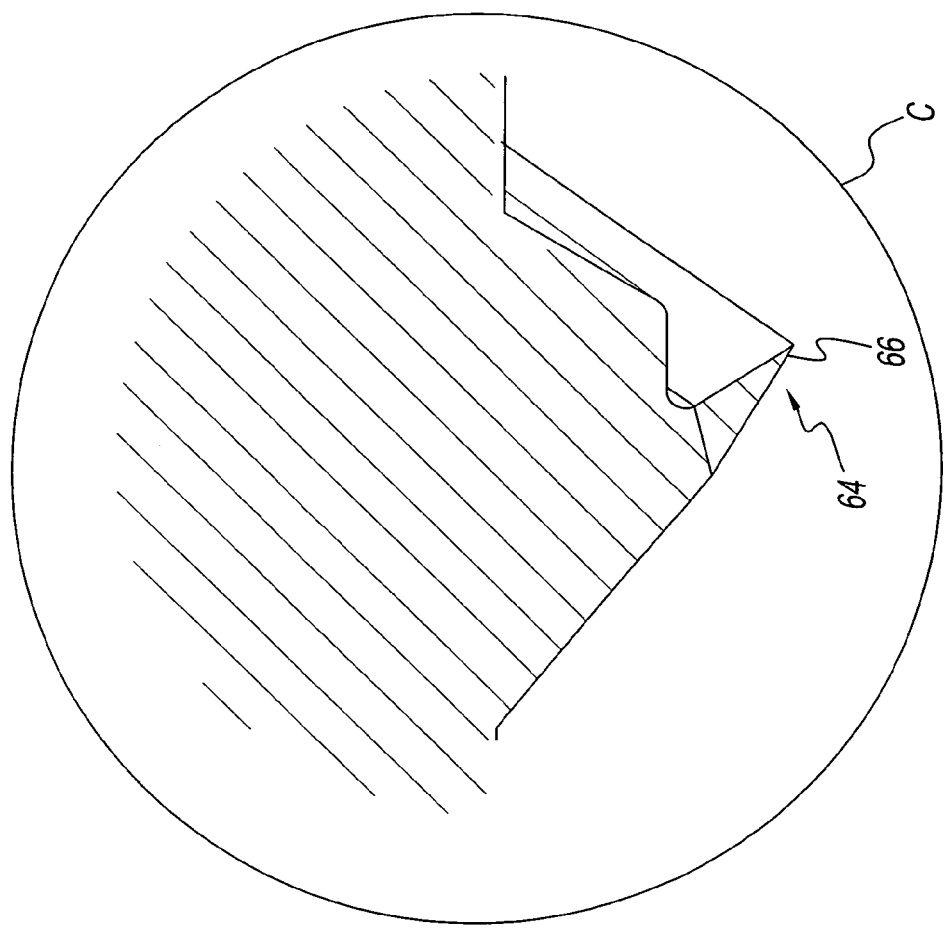

TAMPON INSERTION DEVICE FOR IMPROVED CONTROL AND PLEDGET PLACEMENT

CROSS REFERENCE TO RELATED PATENT APPLICATIONS

This application claims the benefit of U.S. Provisional Application Ser. No. 60/835,638 filed Aug. 4, 2006 entitled "Tampon Insertion Device for Improved Control and Pledget Placement," now pending. The aforementioned application is hereby incorporated herein by reference in its entirety.

BACKGROUND OF THE INVENTION

1. Field of the Invention

The present disclosure relates generally to a tampon applicator assembly. More particularly, the present disclosure relates to an improved tampon applicator assembly that improves user control of the tampon applicator and pledget placement in the body.

2. Description of Related Art

A tampon applicator assembly is used to inject an absorbent or hygienic material, known as a tampon pledget, into a vaginal cavity. Commercial tampon applicator assemblies typically have a barrel and a plunger used to expel a pledget housed in the barrel.

The use of such assemblies requires a user to grip the barrel and guide it easily into the vaginal cavity. This is particularly important since a portion or all of the assembly is out of a direct line of sight of the user during insertion. Accordingly, an assembly that is difficult to grip and/or control can hinder proper and comfortable delivery of the pledget.

Another problem associated with an assembly that is difficult to grip and/or control is that the user often applies excessive gripping force on the barrel to compensate for the lack of grippability. This excessive force may partially deform and damage the barrel and/or plunger, thereby distorting the assembly and obstructing the normal pathway of the pledget therefrom. As a result, the user may be required to apply a significant amount or excess force to eject the pledget from the assembly, which may result in discomfort to the user.

Thus, there is a need to provide improved tampon applicator assemblies, which improve user comfort pledget placement.

SUMMARY OF THE INVENTION

The present disclosure provides an easy to use tampon applicator assembly, which is easy to grip and control during insertion and removal of the applicator assembly, as well as during expulsion of the pledget.

The present disclosure also provides such a tampon applicator assembly having an improved fingergrip.

The present disclosure further provides such a tampon applicator assembly in which the improved fingergrip includes one or more flared portions.

The present disclosure yet further provides such a tampon applicator assembly in which the improved fingergrip includes one or more rib-like gripping structures.

The present disclosure still further provides such a tampon applicator assembly in which the one or more rib-like gripping structures are rings, wavy rings, or combinations thereof.

The present disclosure also provides such a tampon applicator assembly in which the improved fingergrip includes one or more flared portions and one or more rib-like gripping structures.

These and other advantages and benefits of the present disclosure are provided by a tampon applicator assembly having a barrel with an improved fingergrip. The improved fingergrip has one or more flared portions and/or one or more rib-like or ring-like gripping structures. As a result of these features, the tampon assembly provides a user with improved control, which results in proper pledget placement and thus comfort to the user.

A tampon applicator fingergrip is provided that includes a fingergrip portion having a fingergrip surface that is the outermost surface of the fingergrip portion. The fingergrip surface has a virtually uniform radii surface as measured from a centerline of the fingergrip. A flared portion is directly connected to the fingergrip portion. The flared portion has a flare surface that is the outermost surface of the flared portion. The flare surface increases in diameter from the fingergrip surface toward an end of the fingergrip that receives a plunger. The flare surface has a curve represented by an equation range of $y=16.127x^3-1.5061x^2+0.0568x+0.0001$ to $y=6.9136x^3-0.5598x^2+0.0168x+0.0003$, where y is an incremental increase in a height of the curve at a distance along a length of the curve. The x is between 0 to 0.211 inches. The flared portion has a flare diameter between 0.525 inches to 0.575 inches.

A tampon applicator fingergrip is also provided that includes a fingergrip portion having a fingergrip surface that is the outermost surface of the fingergrip portion. The fingergrip surface has a virtually uniform radii surface as measured from a centerline of the fingergrip. A flared portion is directly connected to the fingergrip portion. The flared portion has a flare surface that is the outermost surface of the flared portion. The flare surface increases in diameter from the fingergrip surface toward an end of the fingergrip that receives a plunger. The flare surface has a curve represented by an equation range $y=4.8311x^3-0.1841x^2+0.086x-0.0006$ to $y=3.3937x^3+0.0994x^2+0.014x+0.00004$, where y is an incremental increase in a height of the curve at a distance along a length of the curve. The x is between 0 to 0.250 inches. The flared portion has a flare diameter between 0.450 inches to 0.500 inches.

The above-described and other features and advantages of the present disclosure will be appreciated and understood by those skilled in the art from the following detailed description and drawings.

BRIEF DESCRIPTION OF THE DRAWINGS

FIG. 8 is a side cut away view of FIG. 4 along line AA of the tampon applicator;

FIG. 8a is an exploded view of a wavy ring gripping structure in Area C of FIG. 8;

DETAILED DESCRIPTION OF THE INVENTION

The present disclosure provides a tampon applicator assembly having a barrel with an improved fingergrip. The improved fingergrip has one or more flared portions and/or one or more rib-like or ring-like gripping structures. As a result of these features, the tampon assembly provides a user with improved control, which results in proper pledget placement and thus comfort to the user.

Figure 1:
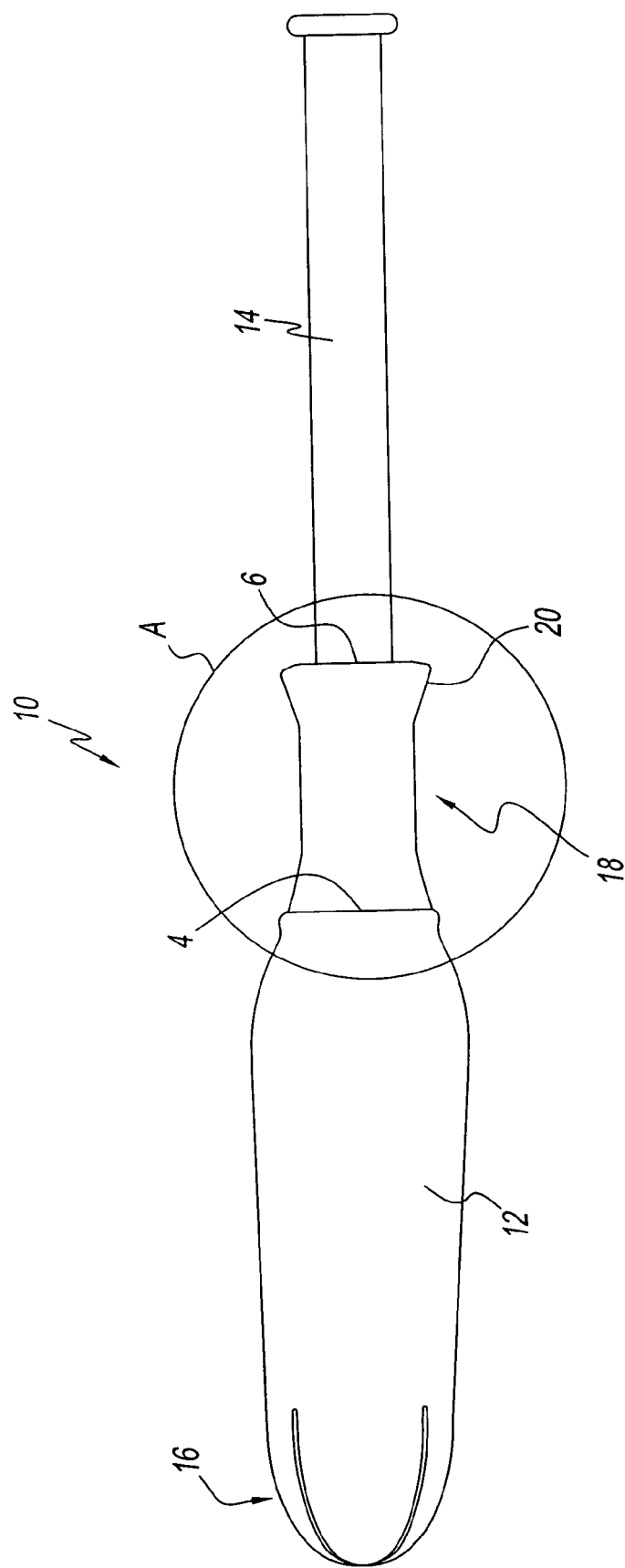
FIG. 1 is a side view of a tampon applicator having a flared fingergrip according to the present disclosure.

Referring to FIG. 1, a tampon applicator with an improved fingergrip according to the present disclosure is represented generally by reference numeral 10. Applicator 10 includes a barrel 12 and plunger 14. Barrel 12 includes an insertion tip 16 and a fingergrip section 18. Fingergrip section 18 includes the improvement of a flared portion 20.

It has been unexpectedly found through consumer testing that fingergrip section 18 with flared portion 20 having an optimal flare angle and/or slope provides enhanced grippability, which results in improved insertion control and tampon pledget placement.

Figure 2:
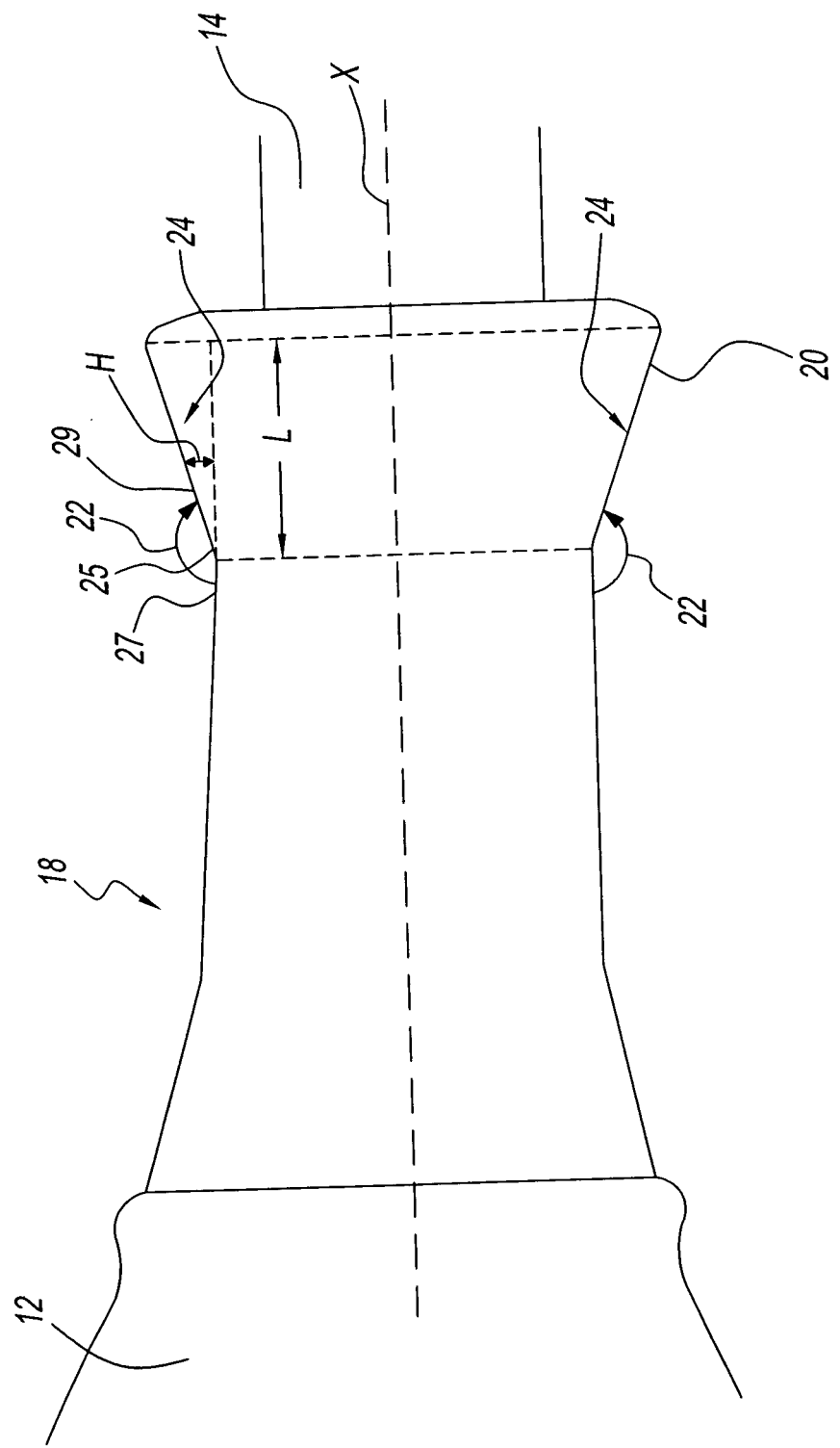
FIG. 2 is an exploded view of area A in FIG. 1 of the flared fingergrip of the present disclosure.

Referring to FIG. 2, an exploded view of area A in FIG. 1 is provided, which details the improved fingergrip section 18 with flared portion 20. Flared portion 20 has a flare angle 22, which is formed at an intersection 25 of fingergrip surface 27 and flare surface 29. Fingergrip surface 27 is a virtually uniformly radii surface as measured from the centerline X of barrel 12. Flare surface 29 has a uniformly enlarging radii, again as measured from the centerline X of barrel 12, thereby resulting in a flare. Flare angle 22, as shown in FIG. 2, is measured from the outer surfaces of surface 27 to flare surface 29.

In addition to flare angle 22, it has been unexpectedly found that when the flared portion 20 has an optimal curve and/or slope 24, enhanced grippability is provided. The optimal curve 24 of flared portion 20 can be determined by measuring the change in the increase of the height H of flared portion 20 at predetermined points over a predetermined length L of the flared portion. Height H is along the radii, while length L is parallel to centerline X.

In one embodiment according to the present disclosure, it has been found that enhanced grippability results from a flare angle 22 between about 139° and about 156° and an optimal curve 24 represented by the equation range of $y=16.127x^3-1.5061x^2+0.0568x+0.0001$ to $y=6.9136x^3-0.5598x^2+0.0168x+0.0003$, where y is the incremental increase in height H of the curve at distance x along the length L of the curve.

In another embodiment according to the present disclosure, it has been found that a flare angle 22 of about 145° and an optimal curve 24 represented by the equation $y=11.27x^3-1.0172x^2+0.024x+0.0002$, provides maximized grippability.

In another embodiment according to the present disclosure, it has been found that a flare angle 22 between about 130° and about 147° and an optimal curve 24 represented by the equation range $y=4.8311x^3-0.1841x^2+0.086x-0.0006$ to $y=3.3937x^3+0.0994x^2+0.014x+0.00004$, provides maximized grippability.

In a further embodiment according to the present disclosure, it has been found that a flare angle 22 of about 140° and an optimal curve 24 represented by the equation $y=1.7529x^3+0.7442x^2-0.0194x+0.0006$, provides maximized grippability.

Tampon applicator 10 with improved fingergrip 20 having the any one of the above-stated flare angles 22 and optimal curves 24 has been found to unexpectedly provide improved guidance, comfort and placement of a tampon pledget in the vaginal vault over those tampon applicators that do not have the improved and novel features according to the present disclosure.

Figure 3:
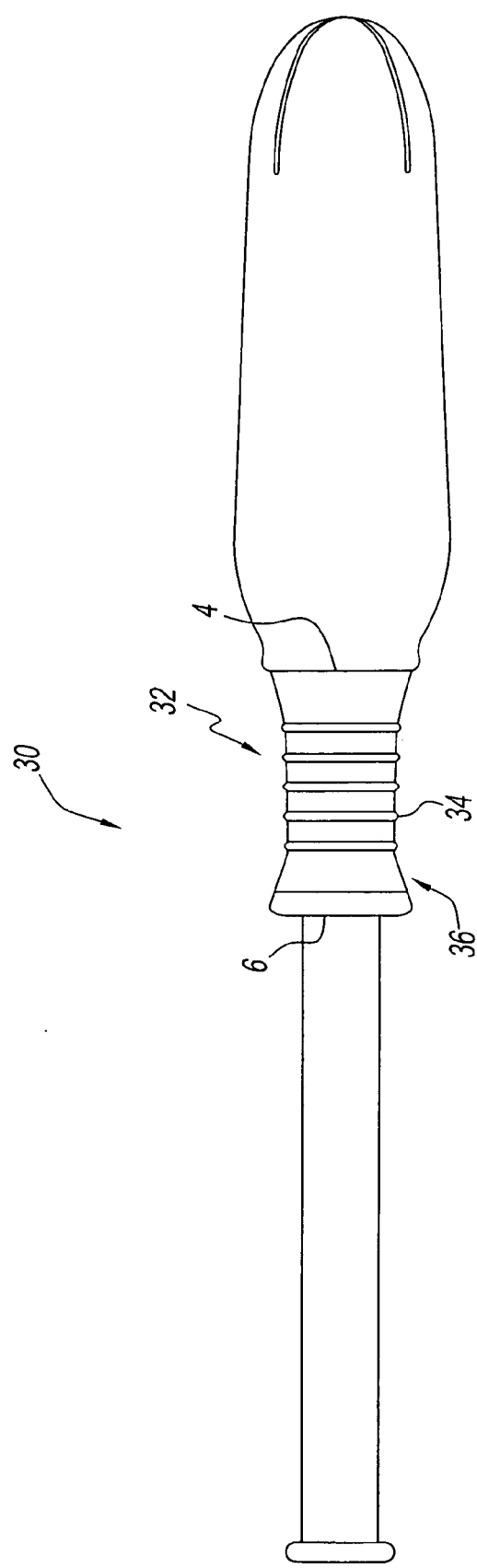
FIG. 3 is a side view of a tampon applicator having a flared fingergrip and a plurality of gripping rings in accordance with the present disclosure.

Referring to FIG. 3, another tampon applicator with an improved fingergrip according to the present disclosure is represented generally by reference numeral 30. Applicator 30 is similar to applicator 10 in FIG. 1 and further includes a fingergrip section 32 having one or more gripping structures 34 and optionally a flared portion 36. Flared portion 36 can have the same optimal curves of flared portions 20 set forth above.

It has been unexpectedly found through consumer testing that fingergrip section 32 having one or more gripping structures 34 provides enhanced grippability, which results in improved insertion control.

The one or more gripping structures 34 may be present in any number. In one embodiment according to the present disclosure, the one or more gripping structures 34 are present in a number or an amount between about two (2) to about six (6). In another embodiment, fingergrip section 32 has five (5) gripping structures 34. In another embodiment, fingergrip section 32 has three (3) gripping structures 34.

It has been unexpectedly determined through extensive research that when 3 gripping structures are used on fingergrip section 32, they should be spaced apart about 0.175 inches to about 0.225 inches for optimal enhancement of grippability. In the embodiments where 3 gripping structures are used, it has been unexpectedly found that each gripping structure has an optimal spacing of about 0.2 inches.

It has been unexpectedly found that when 5 gripping structures are used on fingergrip section 32, they should be spaced apart about 0.075 inches to about 0.125 inches for optimal enhancement of grippability. In the embodiments where 5 gripping structures are used, it has been unexpectedly found that each gripping structure has an optimal spacing of about 0.1 inches.

The one or more gripping structures 34 may be formed in any design or configuration. Suitable configurations include, but are not limited to, ring, wavy ring, discontinuous ring, ribs, or any combinations thereof. Flare is defined as a gradual spreading outward. Fingergrip sections 18 and 32 of FIGS. 1 and 3, respectively, are defined from the plane along edge 4 to barrel free end 6.

Figure 4:
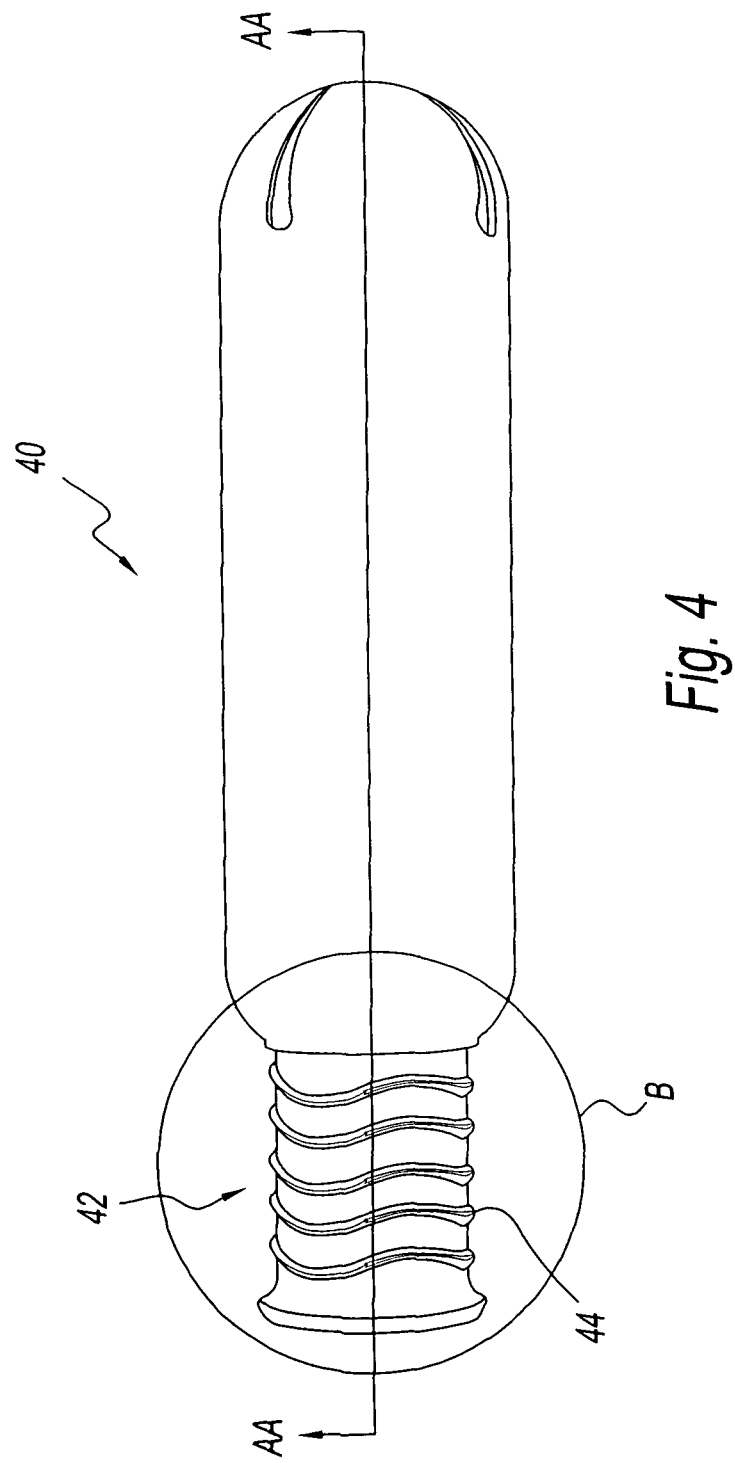
FIG. 4 is a side view of a tampon applicator having a fingergrip section with a plurality of wavy ring gripping structures in accordance with the present disclosure.
Figure 5:
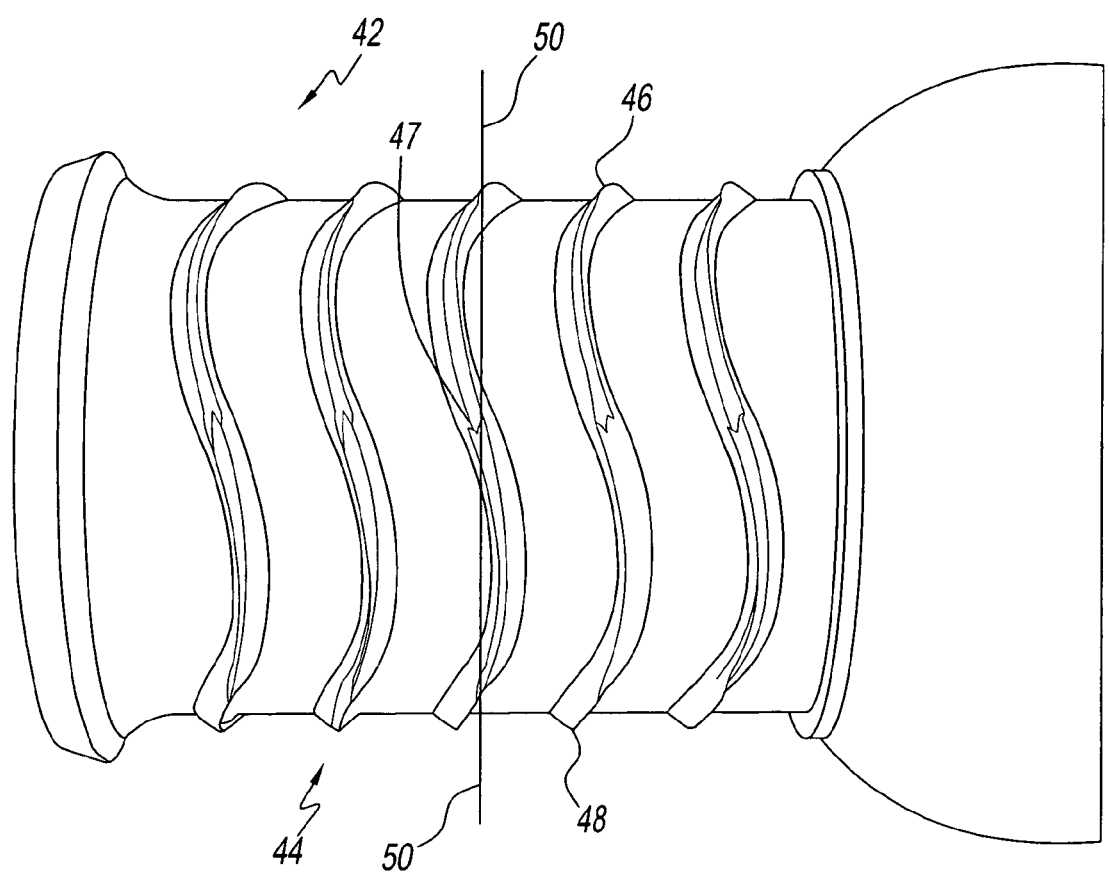
FIG. 5 is an exploded view of area B in FIG. 4 of the fingergrip section with a plurality of wavy ring gripping structures.

Referring to FIG. 4, in one embodiment of the present disclosure tampon applicator 40 has a fingergrip section 42 with one or more wavy ring gripping structures 44. A novel aspect of the one or more wavy rings 44 is that each ring has an oscillating configuration, similar to a sine or cosine wave. As a result, a multi-directional grip is formed. Referring to FIG. 5, which is an exploded view of area B in FIG. 4, on each wavy ring 44, there is a first gripping portion 46 that provides a user with gripping in the insertion direction, a second gripping portion 47 that provides a user with gripping in both the insertion and removal directions, and a third gripping portion 48 that provides a user with gripping in the removal direction.

To achieve the desired enhanced gripping characteristics of the present disclosure, the one or more wavy ring gripping structures 44 should have an amplitude between about 0.01 inches to about 0.04 inches. Amplitude is defined as M in FIG. 6, and is the maximum point of 44 measured to 50. In one embodiment of the present disclosure, the one or more wavy ring gripping structures 44 have an amplitude of about 0.025 inches. The one or more wavy ring gripping structures 44 should have a wavelength between about 0.1 inches to about 0.4 inches. Wavelength is shown as between W to V on 50. In one embodiment of the present disclosure, the one or more wavy ring gripping structures 44 have a wavelength of about 0.25 inches.

Figure 6:
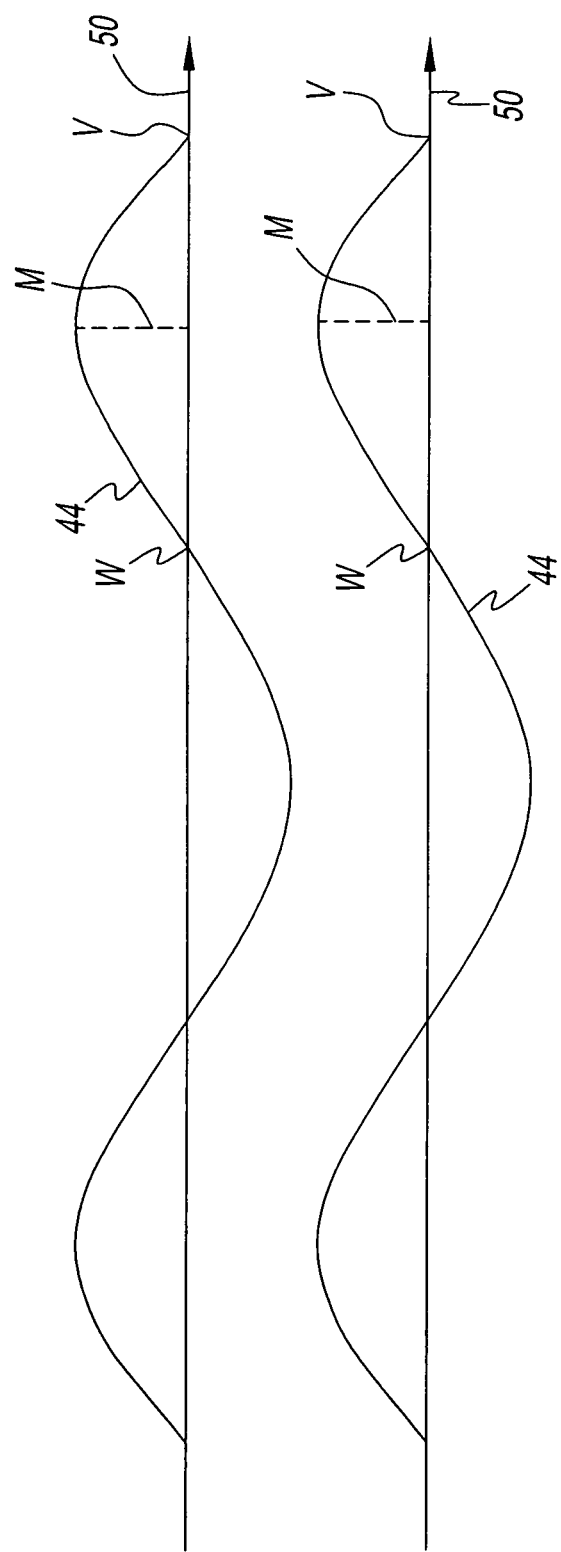
FIG. 6 depicts two wavy ring gripping structures oriented "in phase" in accordance with the present disclosure.
Figure 7:
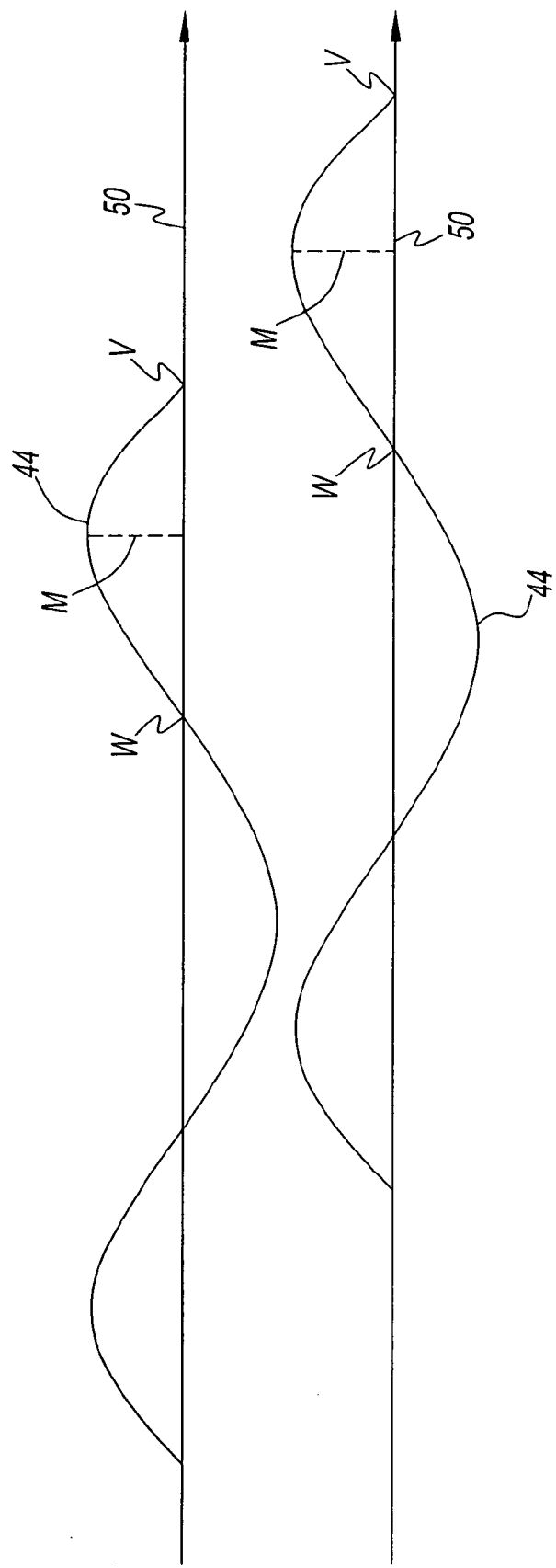
FIG. 7 depicts two wavy ring gripping structures oriented "out of phase" in accordance with the present disclosure.

Referring to FIG. 6, the one or more wavy gripping structures 44 may be orientated "in phase" with respect to centerline 50, thus providing a symmetrical configuration. Referring to FIG. 7, the one or more wavy gripping structures 44 may be orientated "out of phase" with respect to centerline 50. While the gripping structures are shown in a particular orientation in FIG. 7, it should be understood that they can be arranged in any suitable "out of phase" configuration.

Figure 8B:
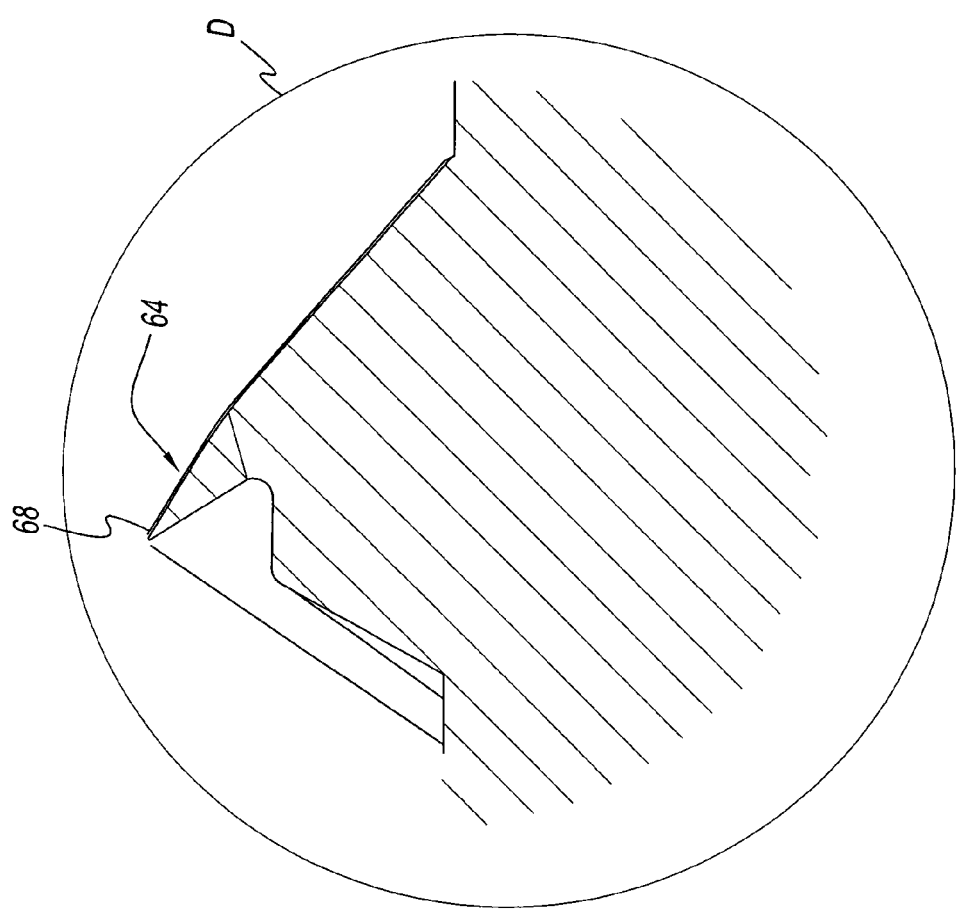
FIG. 8b is an exploded view of a wavy ring gripping structure in Area D of FIG. 8.

Referring to FIG. 8, a cutaway view of the tampon applicator of FIG. 4 along line AA is represented generally by reference numeral 60. Applicator 60 has a fingergrip portion 62 that includes one or more wavy gripping structures 64. Referring to FIG. 8a, an exploded view of one of the wavy gripping structures 64 in area C of FIG. 8 is depicted. Wavy gripping structure 64 has a gripping tail 66, which provides gripping in the removal direction. Referring to FIG. 8b, an exploded view of one of the wavy gripping structures 64 in area D of FIG. 8 is depicted. Wavy gripping structure 64 has a gripping tail 68, which provides gripping in the insertion direction.

In yet another embodiment of the present disclosure, it has been uniquely found that the one or more wavy gripping structures possess distinct gripping features as a result of the molding process. It has been found that a tail portion of the gripping structure is uniquely formed during the molding process when the part is ejected from the mold. During ejection, the mold pulls the soft plastic gripping structure creating the tail of the present disclosure. These distinct gripping features provide additional enhanced, multi-directional gripping ability to the tampon applicator.

Figure 9:
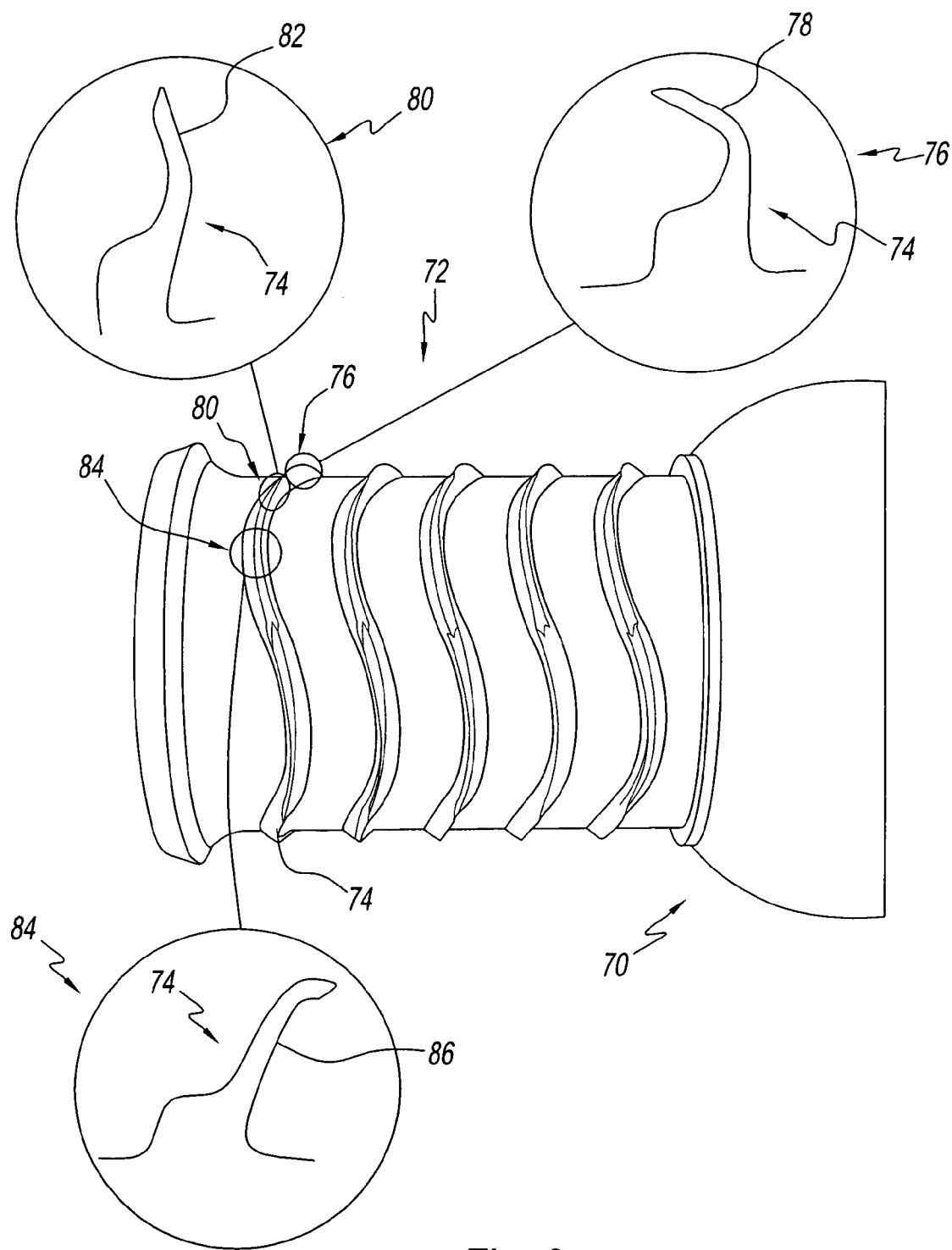
FIG. 9 is an exploded side view of a tampon applicator having a plurality of wavy ring gripping structures and further exploded views of novel features of the wavy ring gripping structures according to the present disclosure.

Referring to FIG. 9, tampon applicator 70 is shown having a finger grip section 72 with one or more wavy gripping structures 74. Each wavy gripping structure 74 is oscillating in a similar manner to a sine or cosine wave. Along each wavy gripping structure 74, the grip alternates in gripping direction, as depicted in the exploded views.

In the case of tampon applicator 70, at the bottom 76 of the wavy gripping structure 74 the wavy gripping structure has a tail 78 that is curved towards the removal end of the applicator. This provides enhanced gripping ability during insertion of the tampon applicator into the vaginal cavity. In the middle 80 of wavy gripping structure 74, the wavy gripping structure has a more upright tail 82 as it begins to oscillate. This more upright tail 78 can advantageously provide gripping ability in both the insertion and removal directions. At the top 84 of wavy gripping structure 74, the wavy gripping structure has a tail 86 that is curved towards the insertion end of the applicator 70. This provides enhanced gripping ability during removal of the tampon applicator from the vagina.

EXAMPLES

Tampon applicators of the Ultra sort having a flared fingergrip according to the present disclosure with a target flare diameter were formed. The flared portion was measured, where y is the incremental increase in height H of the flare at distance x along the length of the flare. The measurements are set forth below in Table 1.

TABLE 1

Flared Fingergrip measurements - Ultra Tampon

| Distance (x axis) | Target Flare Diameter (inches) | | | | |
|---|---|---|---|---|---|
| | 0.525 | 0.535 | 0.550 | 0.565 | 0.575 |
| | | | Y axis | | |
| 0.000 | 0.0000 | 0.0000 | 0.0000 | 0.0000 | 0.0000 |
| 0.025 | 0.0007 | 0.0007 | 0.0004 | 0.0012 | 0.0009 |
| 0.050 | 0.0010 | 0.0011 | 0.0010 | 0.0019 | 0.0015 |
| 0.075 | 0.0010 | 0.0011 | 0.0010 | 0.0037 | 0.0031 |
| 0.100 | 0.0029 | 0.0030 | 0.0035 | 0.0069 | 0.0063 |
| 0.125 | 0.0067 | 0.0069 | 0.0085 | 0.0144 | 0.0147 |
| 0.150 | 0.0143 | 0.0132 | 0.0187 | 0.0283 | 0.0293 |
| 0.175 | 0.0262 | 0.0237 | 0.0354 | 0.0482 | 0.0517 |
| 0.190 | | | | | 0.0663 |
| 0.193 | | | | 0.0630 | |
| 0.200 | 0.0410 | 0.0374 | 0.0537 | | |
| 0.207 | 0.0440 | | | | |
| 0.211 | | 0.0430 | | | |
| Flare angle | 156° | 149° | 145° | 141° | 139° |

Figure 10:
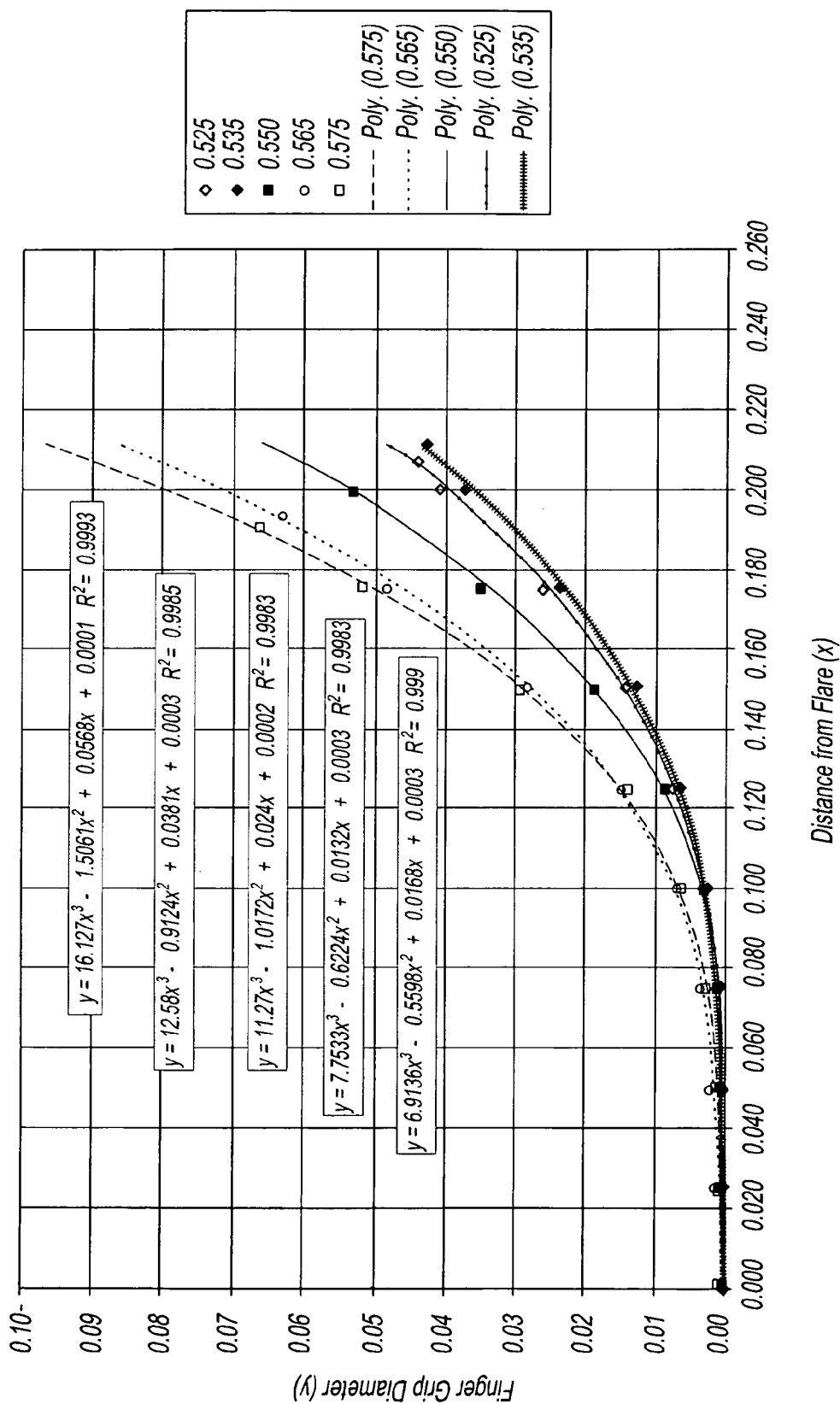
FIG. 10 is a graph representation the curvature of the flared fingergrip for five Ultra tampon applicators according to the present disclosure.

Referring to FIG. 10, the above measurements were plotted on a graph, which details the curvature of the flare of each tampon applicator. Additionally, FIG. 10 indicates the corresponding equation representing each flare.

Tampon applicators of the Regular sort having a flared fingergrip according to the present invention with a target flare diameter were formed. The flared portion was measured, where y is the incremental increase in height H of the flare at distance x along the length of the flare. The measurements are set forth below in Table 2.

TABLE 2

Flared Fingergrip measurements - Regular Tampon

| Distance (x axis) | Target Flare Diameter (inches) | | | | |
|---|---|---|---|---|---|
| | 0.450 | 0.460 | 0.475 | 0.490 | 0.500 |
| | | | Y axis | | |
| 0.000 | 0.0000 | 0.0000 | 0.0000 | 0.0000 | 0.0000 |
| 0.025 | 0.0008 | 0.0031 | 0.0010 | 0.0005 | 0.0014 |
| 0.050 | 0.0013 | 0.0026 | 0.0026 | 0.0014 | 0.0033 |
| 0.075 | 0.0026 | 0.0044 | 0.0046 | 0.0022 | 0.0060 |
| 0.100 | 0.0060 | 0.0080 | 0.0086 | 0.0046 | 0.0106 |
| 0.125 | 0.0102 | 0.0129 | 0.0101 | 0.0100 | 0.0180 |
| 0.150 | 0.0160 | 0.0197 | 0.0208 | 0.0165 | 0.0259 |
| 0.175 | 0.0237 | 0.0284 | 0.0298 | 0.0252 | 0.0354 |
| 0.200 | 0.0341 | 0.0396 | 0.0412 | 0.0370 | 0.0473 |
| 0.225 | 0.0463 | 0.0525 | 0.0549 | 0.0511 | 0.0614 |
| 0.250 | 0.0631 | 0.0689 | 0.0688 | 0.0760 | 0.0869 |
| 0.000 | 0.0000 | 0.0000 | 0.0000 | 0.0000 | 0.0000 |
| 0.025 | 0.0008 | 0.0031 | 0.0010 | 0.0005 | 0.0014 |
| Flare Angle | 147° | 145° | 140° | 135° | 130° |

Figure 11:
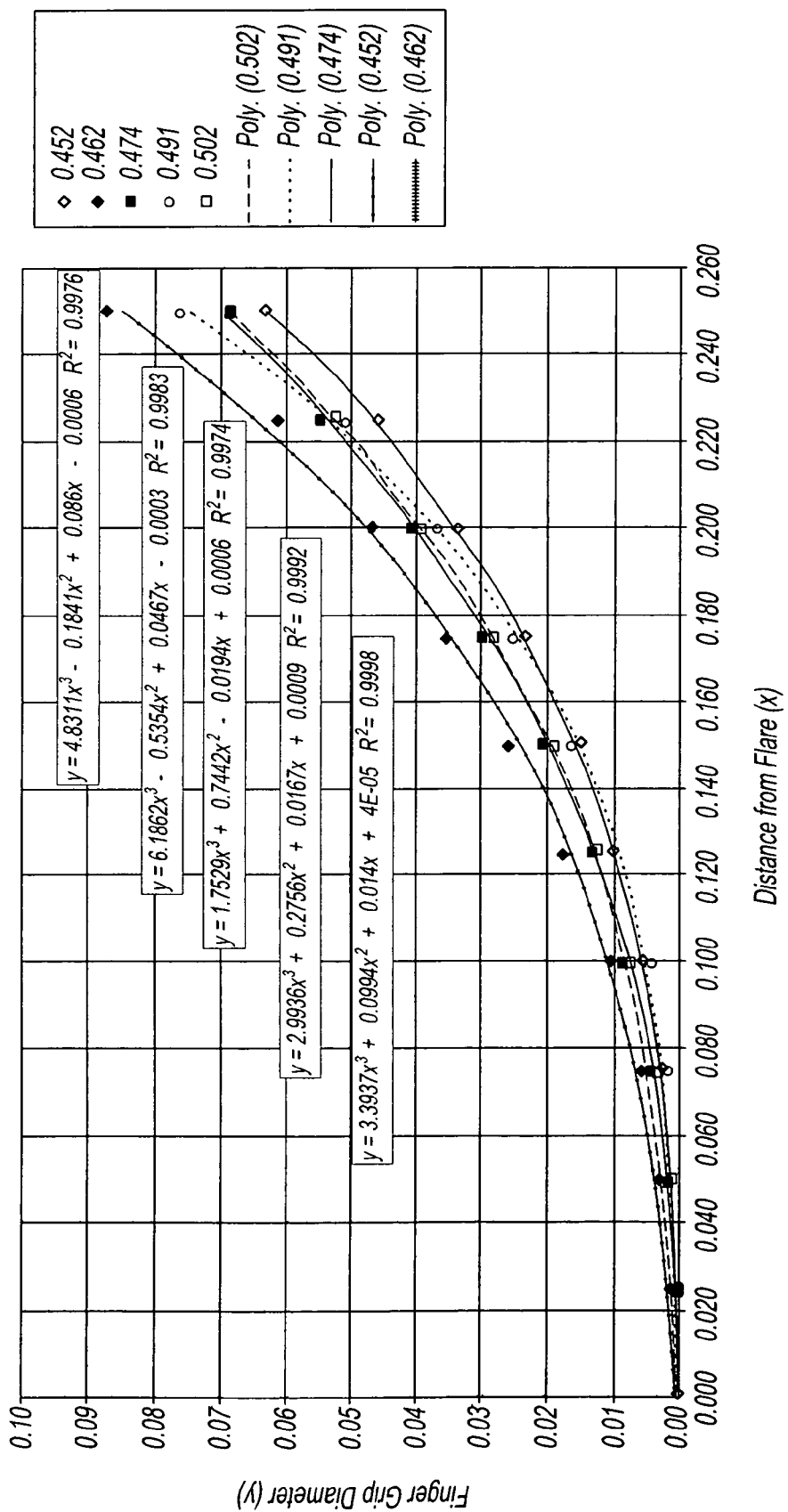
FIG. 11 is a graph representation the curvature of the flared fingergrip for five Regular tampon applicators according to the present disclosure.

Referring to FIG. 11, the above measurements were plotted on a graph, which details the curvature of the flare of each tampon applicator. Additionally, FIG. 11 indicates the corresponding equation representing each flare.

In one embodiment of the present disclosure, a tampon applicator (Applicator 1) having a flared fingergrip with a flare angle between about 139° and about 156° and an optimal curve represented by the equation range of $y=16.127x^3-1.5061x^2+0.0568x+0.0001$ to $y=6.9136x^3-0.5598x^2+0.0168x+0.0003$ was formed. The tampon applicator also had five wavy gripping structures, like those in FIG. 9, spaced from each other at about 0.075 inches to about 0.125 inches.

In another embodiment according to the present disclosure, a tampon applicator (Applicator 2) having a flared fingergrip with a flare angle between about 130° and about 147° and an optimal curve represented by the equation range $y=4.8311x^3-0.1841x^2+0.086x-0.0006$ to $y=3.3937x^3+0.0994x^2+0.014x+0.00004$ was formed. This tampon applicator also had three ring gripping structures, like those in FIG. 3, spaced from each other at about 0.175 inches to about 0.225 inches.

A blind study (n=31) was done comparing tampon applicators according to the present disclosure (Applicator 1 and Applicator 2) to commercially available tampon applicators. The tampons tested are listed below in Table 3 with the corresponding rating on a scale of 1 to 8, with 1 being most preferred and 8 being least preferred.

TABLE 3

Applicator study

| Product Tested | Mean Rating |
| --- | --- |
| Applicator 1 | 2.29 |
| Applicator 2 | 2.61 |
| Playtex Gentle Glide ™ | 3.68 |
| Tampax ™ Pearl | 5.55 |
| Private Label (Dittie) | 5.84 |
| Private label (Walgreen PVL) | 5.94 |
| Kotex Security | 7.58 |

As is evident from the data, the tampon applicators according to the present disclosure were clearly preferred over the commercial products tested. This comes as no surprise since the enhanced properties imparted to a tampon applicator formed according to the present disclosure result in an applicator that has improved grip during use, which results in better control and proper placement of a pledget in the vaginal vault.

We claim:

1. A tampon applicator fingergrip comprising:
   a fingergrip portion having a fingergrip surface that is the outermost surface of said fingergrip portion, said fingergrip surface having a virtually uniform radii surface as measured from a centerline of said fingergrip; and
   a flared portion directly connected to said fingergrip portion, said flared portion having a flare surface that is the outermost surface of said flared portion, said flare surface increasing in diameter from said fingergrip surface toward an end of said fingergrip that receives a plunger, said flare surface also having a curve represented by an equation range of $y=16.127x^3-1.5061x^2+0.0568x+0.0001$ to $y=6.9136x^3-0.5598x^2+0.0168x+0.0003$, where y is an incremental increase in a height of said curve at a distance along a length of said curve, said x being from 0 to 0.211 inches, and said flared portion having a flare diameter from 0.525 inches to 0.575 inches as said x is measured from 0 to 0.211.

2. The tampon applicator fingergrip of claim 1, wherein said curve is represented by the equation $y=11.27x^3-1.0172x^2+0.024x+0.0002$.

3. The tampon applicator fingergrip of claim 1, further comprising one or more gripping structures.

4. The tampon applicator fingergrip of claim 3, wherein said one or more gripping structures have a configuration selected from the group consisting of ring, wavy ring, discontinuous ring, rib, and any combinations thereof.

5. The tampon applicator fingergrip of claim 3, wherein said one or more gripping structures are present in a number between about 2 to about 6.

6. The tampon applicator fingergrip of claim 1, wherein said flared portion is directly connected to an end portion on a side of said flared portion opposite to said fingergrip portion, and wherein said end portion has an end surface that is the entire outermost surface of said end portion that decreases in diameter from said flared portion to said end of said fingergrip that receives said plunger.

7. The tampon applicator fingergrip of claim 1, wherein the tampon applicator fingergrip is on a barrel, wherein said barrel having the tampon applicator fingergrip is entirely positioned about a center axis that is straight, wherein said fingergrip surface is directly connected to a side surface of said barrel, and wherein said side surface extends in an outward curve away from said center axis and is directly adjacent an inward curve that extends inward toward said center axis.

8. A tampon applicator fingergrip comprising:
   a fingergrip portion having a fingergrip surface that is the outermost surface of said fingergrip portion, said fingergrip surface having a virtually uniform radii surface as measured from a centerline of said fingergrip; and
   a flared portion directly connected to said fingergrip portion, said flared portion having a flare surface that is the outermost surface of said flared portion, said flare surface increasing in diameter from said fingergrip surface toward an end of said fingergrip that receives a plunger, said flare surface also having a curve represented by an equation range $y=4.8311x^3-0.1841x^2+0.086x-0.0006$ to $y=3.3937x^3+0.0994x^2+0.014x+0.00004$, where y is an incremental increase in a height of said curve at a distance along a length of said curve, said x being from 0 to 0.250 inches, and said flared portion having a flare diameter from 0.450 inches to 0.500 inches as said x is measured from 0 to 0.250 inches.

9. The tampon applicator fingergrip of claim 8, wherein said curve is represented by an equation $y=1.7529x^3+0.7442x^2-0.0194x+0.0006$.

10. The tampon applicator fingergrip of claim 8, further comprising one or more gripping structures.

11. The tampon applicator fingergrip of claim 10, wherein said one or more gripping structures have a configuration selected from the group consisting of ring, wavy ring, discontinuous ring, rib, and any combinations thereof.

12. The tampon applicator fingergrip of claim 10, wherein said one or more gripping structures are present in a number between about 2 to about 6.

* * * * *